(12) United States Patent
Chaung et al.

(10) Patent No.: US 7,588,788 B2
(45) Date of Patent: Sep. 15, 2009

(54) IMMUNE MODULATION AND ANTI-ALLERGY ACTIVITIES OF ZINGIBER ZERUMBET

(75) Inventors: Hso-Chi Chaung, PingTung (TW);
Chung-Sheng Huang, Taipei (TW);
Fun-Ya Lee, Taipei (TW);
Tsung-Chung Lin, Fullerton, CA (US)

(73) Assignee: Wholesome Life Science Co., Ltd., Taipei (TW)

( * ) Notice: Subject to any disclaimer, the term of this patent is extended or adjusted under 35 U.S.C. 154(b) by 351 days.

(21) Appl. No.: 11/184,678

(22) Filed: Jul. 18, 2005

(65) Prior Publication Data
US 2006/0083799 A1    Apr. 20, 2006

Related U.S. Application Data

(60) Provisional application No. 60/590,552, filed on Jul. 23, 2004.

(51) Int. Cl.
*A61K 36/906* (2006.01)
*A61K 36/00* (2006.01)
(52) U.S. Cl. .................. 424/756; 424/725
(58) Field of Classification Search .......... None
See application file for complete search history.

(56) References Cited

U.S. PATENT DOCUMENTS

| | | | |
|---|---|---|---|
| 5,401,777 A * | 3/1995 | Ammon et al. | 514/731 |
| 5,686,442 A * | 11/1997 | Ohtsuka et al. | 514/211.04 |
| 5,925,615 A * | 7/1999 | Kern et al. | 510/463 |
| 6,027,728 A * | 2/2000 | Yuen | 424/728 |
| 6,264,928 B1 * | 7/2001 | Jean et al. | 424/65 |
| 6,383,525 B1 * | 5/2002 | Hsu et al. | 424/728 |
| 6,576,267 B2 * | 6/2003 | Gelber et al. | 424/725 |
| 6,730,332 B2 * | 5/2004 | Agarwal et al. | 424/769 |
| 2004/0028756 A1 * | 2/2004 | Teather et al. | 424/752 |
| 2005/0118287 A1 * | 6/2005 | Jean et al. | 424/756 |

FOREIGN PATENT DOCUMENTS

| JP | 09-087193 | * | 3/1997 |
| JP | 09-330243 | * | 12/1998 |
| JP | 01-221344 | * | 9/1999 |
| JP | 2000-159626 | * | 6/2000 |
| JP | 2000-336017 | * | 12/2000 |
| JP | 2003-070442 | * | 3/2003 |

OTHER PUBLICATIONS

Ozaki et al. Shoyakugaku Zasshi. 1988. vol. 42, No. 4, pp. 333-336, BIOSIS Abstract enclosed.*
Somchit et al. Indian J. Pharmacol. June 2003. vol. 35, No. 3, pp. 181-182.*

(Continued)

*Primary Examiner*—Christopher R. Tate
(74) *Attorney, Agent, or Firm*—Cohen Pontani Lieberman & Pavane LLP (57) ABSTRACT

The present invention provides for a method of preparing a nutraceutical formulation comprising the step of solvent extraction from the root of *Zingiber zerumbet* Sm, and the use of this formulation to regulate the immune system, and more specifically to prevent or to treat an allergic disorder.

7 Claims, 6 Drawing Sheets

OTHER PUBLICATIONS

Wenzel, S.E., The role of leukotrienes in asthma. *Prostaglandins Leukot Essent Fatty Acids* 2003; 69:145-55.

Leff, A R., Regulation of leukotrienes in the management of asthma: biology and clinical therapy. *Annu Rev Med* 2001; 52:1-14.

Aizawa et al., Eosinophil and neutrophil production of leukotriene C4 and B4: comparison of cells from asthmatic subjects and healthy donors. *Ann Allergy* 1990; 64:287-92.

Davern, T.J et al., Leukotriene antagonists. Clin. Liv. Dis. 2003; 7(2):501-512.

Beghe B, Barton S, Rorke S, Peng Q, Sayers I, Gaunt T, Keith T, Clough J, Holgate S, Holloway J. Polymorphisms in the interleukin-4 and interleukin-4 receptor alpha chain genes confer susceptibility to asthma and atopy in a Caucasian population. *Clin Exp Allergy* 2003; 33:1111-1117.

Shirai T, Suzuki K, Inui N, Suda T, Chida K, Nakamura H. Th1/Th2 profile in peripheral blood in atopic cough and atopic asthma. *Clin Exp Allergy* 2003;33:84-9.

Lee YC, Lee KH, Lee HB, Rhee YK. Serum levels of interleukins (IL)-4, IL-5, Il-13, and interferon-gamma in acute asthma. *J Asthma* 2001; 38:665-71.

Kalin P. The Common Butterbur (Petasites hybridus)—Portrait of a Medicinal Herb. *Forsch Komplementarmed Klass Naturheilkd* 2003; 10 Suppl 1:41-4.

Vimala S, Norhanom AW, Yadav M. Anti-tumour promoter activity in Malaysian ginger rhizobia used in traditional medicine. *Br J Cancer* 1999; 80:110-6.

Murakami A, Takahashi D, Kinoshita T, Koshimizu K, Kim HW, Yoshihiro A, Nakamura Y, Jiwajinda S, Terao J, Ohigashi H. Zerumbone, a Southeast Asian ginger sesquiterpene, markedly suppresses free radical generation, proinflammatory protein production, and cancer cell proliferation accompanied by apoptosis: the alpha,beta-unsaturated carbonyl group is a prerequisite. *Carcinogenesis* 2002; 23:795-802. Comment in: Carcinogenesis 2002; 23:1961; author reply 1963.

Oliveros et al., Pharmacognostic Studies on Zingiber zerumbet and its Proposed Variety (Family Zingiberaceae), *Int. J. Crude Drug. Res.*, 20 (1982), No. 3, pp. 141-153.

Somchit M. Nhareet et al., Anti Inflammatory Prolperty of?Ethanol and Water Extracts of Zingiber Zerumbet, *Indian Journal of Pharmacology* (2003); 35:181-182.

Murakami et al., Effects of Selected Food Factors with Chemopreventive Properties on Combined Lipopolysaccharide-and interferon-γ-induced IκB degradation in RAW264.7 Macrophages, *Cancer Letters* 195 (2003) 17-25 XP009099883.

* cited by examiner

Figure 1.

```
   1 gatagctgcc atcggctgac ctagagaaga cacatcagct gatcctttgg accctctgac
  61 ttgagacaga agttctgggc ttctcctcct gcggcctagc tctgagacaa tgaacgctac
 121 acactgcatc ttggctttgc agctcttcct catggctgtt tctggctgtt actgccacgg
 181 cacagtcatt gaaagcctag aaagtctgaa taactatttt aactcaagtg gcatagatgt
 241 ggaagaaaag agtctcttct tggatatctg gaggaactgg caaaaggatg gtgacatgaa
 301 aatcctgcag agccagatta tctctttcta cctcagactc tttgaagtct gaaagacaa
 361 tcaggccatc agcaacaaca taagcgtcat tgaatcacac ctgattacta ccttcttcag
 421 caacagcaag gcgaaaaagg atgcattcat gagtattgcc aagtttgagg tcaacaaccc
 481 acaggtccag cgccaagcat tcaatgagct catccgagtg gtccaccagc tgttgccgga
 541 atccagcctc aggaagcgga aaaggagtcg ctgctgattc ggggtgggga agagattgtc
 601 ccaataagaa taattctgcc agcactattt gaatttttaa atctaaacct atttattaat
 661 atttaaaact atttatatgg agaatctatt ttagatgcat caaccaaaga agtatttata
 721 gtaacaactt atatgtgata agagtgaatt cctattaata tatgtgttat ttataatttc
 781 tgtctcctca actatttctc tttgaccaat taattattct ttctgactaa ttagccaaga
 841 ctgtgattgc ggggttgtat ctgggggtgg gggacagcca agcggctgac tgaactcaga
 901 ttgtagcttg tacctttact tcactgacca ataagaaaca ttcagagctg cagtgacccc
 961 gggaggtgct gctgatggga ggagatgtct acactccggg ccagcgcttt aacagcaggc
1021 cagacagcac tcgaatgagt caggtagtaa caggctgtcc ctgaaagaaa gcagtgtctc
1081 aagagacttg acacctggtg cttccctata cagctgaaaa ctgtgactac acccgaatga
1141 caaataactc gctcatttat agtttatcac tgtctaattg catatgaata aagtatacct
1201 ttgcaacc
```

Figure 2.

```
  1 cttaattgtc tctcgtcact gacggcacag agctattgat gggtctcaac cccagctag
 61 ttgtcatcct gctcttcttt ctcgaatgta ccaggagcca tatccacgga tgcgacaaaa
121 atcacttgag agagatcatc ggcattttga acgaggtcac aggagaaggg acgccatgca
181 cggagatgga tgtgccaaac gtcctcacag caacgaagaa caccacagag agtgagctcg
241 tctgtagggc ttccaaggtg cttcgcatat tttatttaaa acatgggaaa actccatgct
301 tgaagaagaa ctctagtgtt ctcatggagc tgcagagact ctttcgggct tttcgatgcc
361 tggattcatc gataagctgc accatgaatg agtccaagtc cacatcactg aaagacttcc
421 tggaaagcct aaagagcatc atgcaaatgg attactcgta gtactgagcc accatgcttt
481 aacttatgaa ttttaatgg ttttattttt aatatttata tatttataat tcataaaata
541 aaatatttgt ataatgtaac agaaaaaaaa aaaaaaaaaa aaaa
```

Chemical Name: zerumbone

Autoname: 2,6,9,9-tetramethyl-cycloundeca-2,6,10-trienone

Molecular Formula   $C_{15}H_{22}O$

Molecular Weight 218.34

Figure 6.

IMMUNE MODULATION AND ANTI-ALLERGY ACTIVITIES OF ZINGIBER ZERUMBET

PRIORITY CLAIM

Priority is claimed on the following application: Country: U.S., application Ser. No.: 60/590,552, Filed: Jul. 23, 2004, the content of which is incorporated here by reference.

BACKGROUND OF THE INVENTION

1. Field of the Invention

The present invention provides for a novel nutraceutical formulation comprising an extract of the root zingiber zerumbet Sm, and the use of the same to regulate the immune system.

2. Description of the Related Art

Leukotrienes (LT), specifically the cysteinyl LTs, LTC4, LTD4 and LTE4, have been implicated in the clinical course, physiologic changes, and pathogenesis of asthma (1). LTC4, LTD4 and LTE4 are potent bronchoconstrictors and involve in additional effects on blood vessels, mucociliary clearance and eosinophilic inflammation (2). In addition, the cysteinyl LTs are formed from cells commonly associated with asthma, including eosinophils and mast cells (3). Therefore, leukotriene receptor antagonists are being used widely in the treatment of bronchial asthma. However, the published data regarding liver injury related to a novel group of asthma drugs, typically leukotriene receptor antagonists, are in heightened awareness of hepatotoxicity (4). Thus, herbs open a new window for having medicative potential on long-term therapy of asthma. The $T_h$ cell cytokines by peripheral blood T cells have been found to correlate with asthma severity. Recent research showed that interleukin-4☐IL-4☐binding to its receptor (IL-4R) is essential for the development of airway inflammation present in asthma (5). A significantly lower ratio of IFN-gamma-/IL-4-producing CD4+ T cells after 12-O-tetradecanoylphorbol-13-acetate (TPA)/ionomycin stimulation was found in patients with atopic cough and atopic asthma compared with normal subjects, and the proportion of IL-4-producing CD4+ T cells was significantly higher in patients with atopic asthma than in normal control subjects (6). As compared with control human subjects, acute asthmatics had significantly increased levels of circulating IL-4 ($p<0.001$), IL-5 ($p<0.001$), and IL-13 ($p<0.001$), although the differences were of borderline significance in serum IFN-gamma ($p=0.069$) (7). However, the extremely low serum levels of these cytokines were merely detectable in animal studies. A new cheap biotech examination, quantitative competitive reverse transcriptase-polymerase chain reaction (qc-RT-PCR), was therefore developed in our lab to quantify gene expressions of cytokines in immune cells in order to precisely evaluate the therapeutic indications of traditional herbs. As searching potential medicative herb, competitive cysteinyl leukotriene receptor antagonist has been considered as a new class of asthma medications (8). Zingiber zerumbet Smith has recently been found to have anti-tumor promoter activity (9) and markedly diminished inducible nitric oxide synthase (iNOS) and cyclooxygenase 2 (COX-2), together with the release of tumor necrosis factor-alpha (TNF-α) in mouse macrophages (10).

SUMMARY OF THE INVENTION

Here we demonstrate that Zingiber zerumbet has beneficial effects of inhibiting the release of inflammatory mediators and influencing the gene expressions of cytokine network. Examples of human use of extracts of Zingiber zerumbet to treat allergic disorders were also described.

The potentials of the aqueous crude extract (ACE) of Zingiber zerumbet (L.) Smith (ZZ) in anti-hypersensitivity and anti-inflammation were demonstrated in mice. Leukotriene C4 (LTC4) release was measured from lung tissue of mice treated with ZZ-ACE. Results showed that ZZ-ACE effectively suppressed LTC4 release from the lung tissue. An active compound was identified as 5,7-Dihydroxy-2-(4-hydroxy-phenyl)-3-methoxy-chromen-4-one for the effect of suppressing LTC4.

Ova-albumin was used to induce asthmatic allergy reactions in mice. Mice treated with ZZ-ACE had higher ratios of splenocyte IFN-γ/IL-4 gene expressions levels ($p<0.05$) as compared with those of the control groups. Zerumbone was identified as an active ingredient to increase the IFN-γ/IL-4 gene expression ratio.

Anti-allergic effects were also observed when human volunteers were administrated with ZZ-ACE in liquid or in capsule form.

These results indicate that extracts of ZZ, using ethanol, water, or a mixture of ethanol and water as solvent, contains components that have potentials in preventing or treating allergic inflammation.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

DETAILED DESCRIPTION OF THE PRESENTLY PREFERRED EMBODIMENTS

Materials and Methods

Equipment: Silica gel (Merck Kieselgel 60, 230-400 mesh ASTM) for column chromatography, and PLC (0.5 mm, Merck Kieselgel 60 F254) were from Merck; proton NMR spectrum was measured by Varians 500 and Mass spectrum by Applied LC-MS.

ZZ-ACE as a water extraction: 50 g of dried root of *Zingiber zerumbet* (L.) Smith was mixed with 500 ml distilled water (10 folds weight) and refluxed for 4 hours at 100° C. The extract was filtered and concentrated to 100 ml and was then freeze-dried. The freeze-dried powder was stored as aqueous crude extract (ACE) of *Zingiber zerumbet* (L.) Smith, or ZZ-ACE.

Ethanol extraction: Dried ZZ was crushed and mixed with 10 fold of ethanol (10 ml ethanol per gZZ) and refluxed at 60° C. for 4 hrs. The extract was filtered and concentrated to 1/10 volume before was freeze-dried and stored as Ethanol Extract. The Ethanol Extract was further partially purified using silica gel column.

Column Chromatography: The ethanol extract (65 g) was concentrated and applied onto the column chromatography ($SiO_2$, 7.5 cm ID×20 cm H). The solvent step-gradient was initiated with n-Hexane/ethyl acetate (or n-Hex/EA) (1000 ml/200 ml), followed by n-Hex/EA (600 ml/400 ml), n-Hex/EA (400 ml/600 ml), EA (1000 ml), and finally methanol (1000 ml), consecutively. The eluent was collected 500 ml/flask from the beginning and the flow rate was about 30 ml/min. Twelve fractions were collected and named as NP1 to NP12 following the elution order.

Isolation of zerumbone: Content in fraction NP2 was re-crystallized with methanol to obtain a pure crystal. Results form proton NMR and MS spectra experiment determined the chemical as zerumbone (0.8 g). Fraction NP2 was named as Crude Zerumbone.

Preparation of a Crude Flavnoid fraction: NP12 (5 g) was applied onto another column ($SiO_2$, 2.5 cm ID×12 cm H). The eluent was collected 200 ml per fraction from the beginning and the flow rate was about 10 ml/min. The solvent gradient was n-Hex (100 ml), n-Hex/EA (100 ml/100 ml), n-Hex/EA (100 ml/150 ml), EA (100 ml), and EA/MeOH (100 ml/50 ml), consecutively. Seven flasks were collected and named as NP12-1 to NP12-7. Fraction NP12-3 was named as Crude Flavnoid.

Isolation of 5,7-dihydroxy-2-(4-hydroxy-phenyl)-3-methoxy-chromen-4-one: NP12-3 (30.2 mg) was isolated and applied onto the PLC developed with dichloromethane/methanol (30/1) to obtain eight strips (NP12-3-1 to NP12-3-8). Materials from strip NP12-3-3 (3.4 mg, named as PLC Purified Flavnoid, 90% pure) was isolated and re-crystallized with n-Hex/acetone. The pure flavone analogue (1.5 mg) was obtained and identified with proton NMR (Varians 500) and LC-Mass spectra as 5,7-dihydroxy-2-(4-hydroxy-phenyl)-3-methoxy-chromen-4-one.

Experiment 1: Anti-Pulmonary Inflammatory Activities of an Aqueous Crude Extract (ACE) of *Zinqiber zerumbet* (L.) Smith in Mice Methods of Experiment 1:

Animal handling, drug treatment, and lung tissue sample collection: A total of 20 female ICR mice, 4 weeks old, were obtained from the National Laboratory Animal Center (Taipei, Taiwan). Mice were randomized into two groups, the control group and the ZZ-ACE group. Mice in the control group drank water and those in the ZZ-ACE group drank aqueous crude extract (ACE) of *Zingiber zerumbet* (L.) Smith (ZZ-ACE, 28.8 mg/ml) filtered with 0.22 μm filter. All mice were fed ad lib. After 28 days of feeding, all mice were anesthetized with sodium pentobarbital. 20 ml of Tyrode's buffer was used to perfuse the lung. After the perfusion, 0.5 g of lung tissue was taken from the same portion of each lung. Lung tissues were chopped with No.11 surgical blade, and then incubated in 10 ml Tyrode's buffer with 95% $O_2$ at 37° C. for 45 minutes. After the incubation, leukotriene $C_4$ in the medium was purified with a C18 cartridge and then quantified by a leukotriene $C_4$ EIA kit (Cayman Chemical Company, MI, USA).

Results of Experiment 1: Anti-Pulmonary Inflammatory Activities of ZZ-ACE

Anti-pulmonary inflammatory activities of ZZ-ACE in mice: Lung tissue of mice in ZZ-ACE group released significantly lower amount of Leukotriene $C_4$ (Table1). Since LTC4 was named as the "slow-reactant of anaphylaxis", the reduced production of Leukotriene $C_4$ indicates the medicative effects of ZZ-ACE.

TABLE 1

Level of LTC4-release from the lung tissue of mice fed with or without ZZ-ACE

|  | Control | ZZ-ACE | P-value |
|---|---|---|---|
| LTC4 (pg/lung) | 429 (100%) | 261 (61%) | 0.027* |

*compared to control, significantly different ($P < 0.05$).

Experiment 2: Identification of an Anti-Inflammation Compound as 5,7-dihydroxy-2-(4-hydroxy-phenyl)-3-methoxy-chromen-4-one Method of Experiment 2: Identification of an Anti-Inflammation Compound Cell culture and drug treatment: Rat Basophilic Leukemia-1 (RBL-1) was purchased from Food Industry Research and Development Institute (CCRC 60198, ATCC CRL-1378), and cultured in MEM-alpha medium (Gibco, 12000). All trans-retinoic acid (1 μg/ml) was added to a 3.5 cm diameter well (6-well plate) at $2 \times 10^6$ cells/2 ml/well. Plates were then incubated at 37° C. with 5% $CO_2$ in air for 16 hr. Various volumes of ZZ samples were added to the wells to make the appropriate final concentrations (0, 0.5, 5, 50 μg/ml) and incubated for 2 more hours. A23187 (calcium ionophore) was added to each well to reach the final concentration of 10 μM to stimulate RBL-1 cells to release LTC4/cLTs for 15 min. The mediums in the wells were centrifuged at 5000 rpm for 10 min to obtain the supernatant for ELISA assay.

LTC4/cLTs ELISA assay: The supernatants of the cell cultures were diluted into appropriate concentrations before the EIA analysis for LTC4/cLTs. Analysis was performed according to the procedures provided by the manufacturer.

MTT [3-(4,5-dimethylthiazol-2-yl)2,5-diphenyltetrazolium bromide] assay: To determine cell viability, cultured medium were removed, and cells were washed with 1×PBS. Then MTT (Sigma, M2128) added to the 96-well plate to reach a concentration of 0.5 mg/ml. After 4 h incubation at 37° C., the plate was added with 150 μl of acidic isopropanol (0.1N HCl) per well to dissolve purple crystal. After overnight incubation, OD was determined by using a micro plate reader at 560 nm.

Results of Experiment 2: Identification of an Anti-Inflammation Compound

Figure 1:
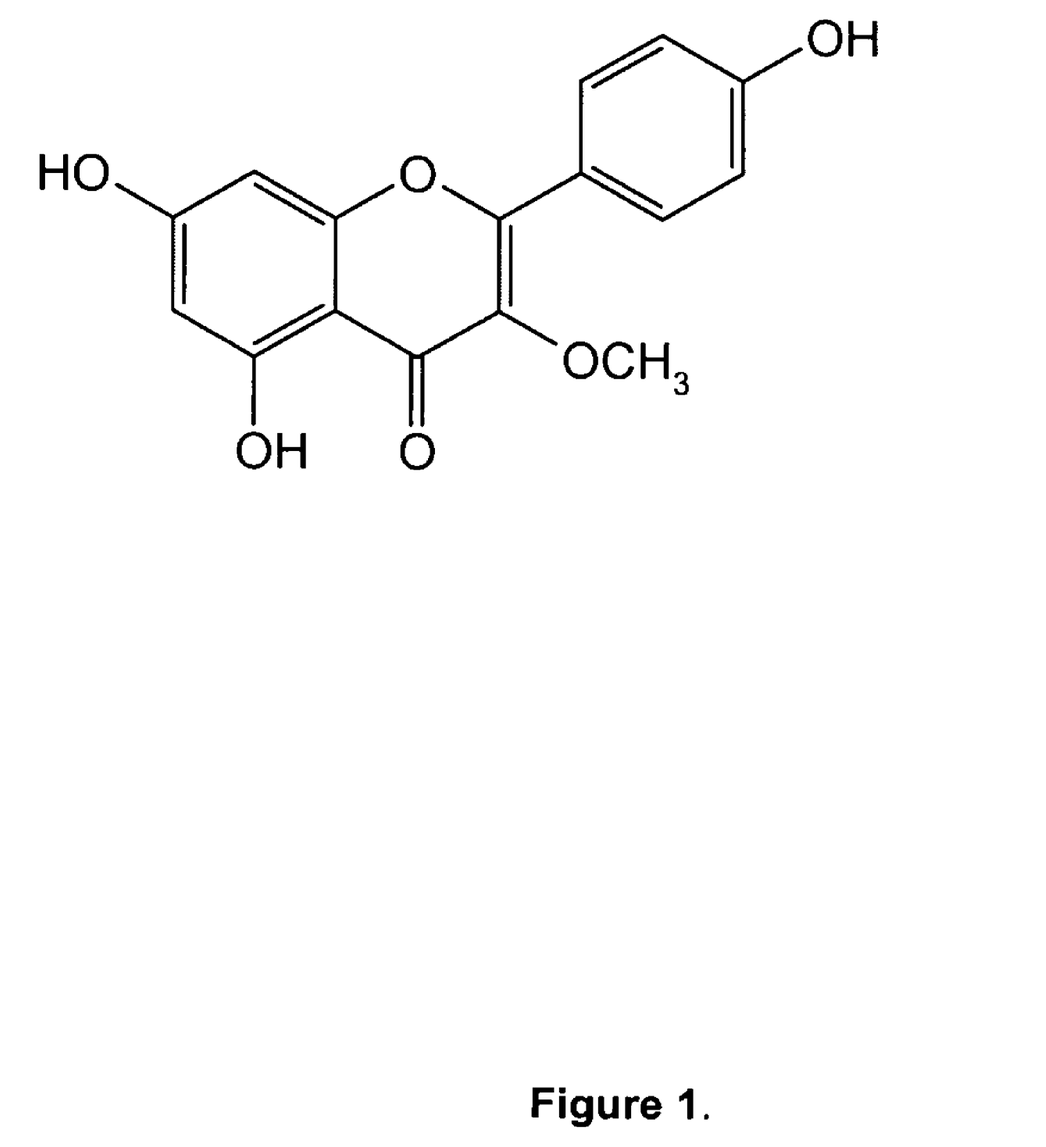
FIG. 1 is the chemical structure of 5,7-Dihydroxy-2-(4-hydroxy-phenyl)-3-methoxy-chromen-4-one.

Both Crude Flanvoid Fraction and an Identified Flavnoid reduce CLTs/LTC4 secretion by A23187 stimulated Rat Basophilic Leukemia-1 (RBL-1) cell: Tables 2A and 2B showed that compared to control, both the ZZ Ethanol Extract and Crude Flavnoid fractions effectively reduced the CLTs and CLT4 secretion of leukemia cells tested. The fraction which showed to have the highest activity was identified to contain a major flavnoid, about 90% pure. The structure of the flavnoid was determined to be:

5,7-dihydroxy-2-(4-hydroxy-phenyl)-3-methoxy-chromen-4-one. (see FIG. 1).

TABLE 2A

Effects of ZZ samples on cell viability and level of CLTs released by A23187 stimulated leukemia cells

|  | Control, no ZZ | Ethanol Extract (0.5 μg/ml) | Crude Flavnoid (5 μg/ml) |
| --- | --- | --- | --- |
| % CLTs vs. control | 100 | 46 | 17 |
| Viability (MTT %) | 100 | 90 | 74 |

TABLE 2B

Effects of ZZ samples on cell viability and level of LTC4 released by A23187 stimulated leukemia cells

|  | Control, no ZZ | Crude Flavnoid (5 μg/ml) | Crude Flavnoid (50 μg/ml) | PLC Purified Flavnoid (50 μg/ml) |
| --- | --- | --- | --- | --- |
| % LTC4 vs. control | 100 | 63 | 36 | 6 |
| Viability (MTT %) | 100 | 83 | 87 | 65 |

Experiment 3: Anti-Allergic Activities of ZZ-ACE, Using Mice Model

Methods of Experiment 3: Anti-Allergic Activities of ZZ-ACE, Mice Model, Ex Vivo Animal handling, treatment, and spleen cell harvesting: A total of 24 female ICR mice from the National Laboratory Animal Center (Taipei, Taiwan) were randomized into three groups: the negative control group (n=4), the parallel control group (n=7) and the ZZ-ACE group (n=10). Mice in the negative control group were fed ad lib without any treatment. Mice in the parallel control group and the ZZ-ACE group were fed with water or ZZ-ACE, respectively, for 56 days, while undergone a scheduled induced asthmatic reaction. Asthmatic reaction was induced by first sensitizing the mice with I.P. administration of 20 μg ovalbumin and 2 mg aluminum hydroxide in 100 μl of 0.9% saline per mouse, starting on day 42 for three consecutive days, and then the allergic asthma was induced by dropping 10 μl of aerosol with 1% ovalbumin into the trachea of each mouse. Twenty minutes after asthma was induced, mice were sacrificed. Mice spleen cells were isolated by mechanical disruption, and hypotonic lysis of erythrocytes was undertaken in cell suspension. Spleen cells were stimulated with or without 12 μg Con A/$2\times10^6$ cells/well (Sigma Chemical, St. Louis, Mo., USA) at 37° C. for 24 hours. Total RNA samples were isolated from cultured splenocytes, and were evaluated by quantitative competitive-RT-PCR (qc-RT-PCR) to determine their gene expression levels.

Figure 2:
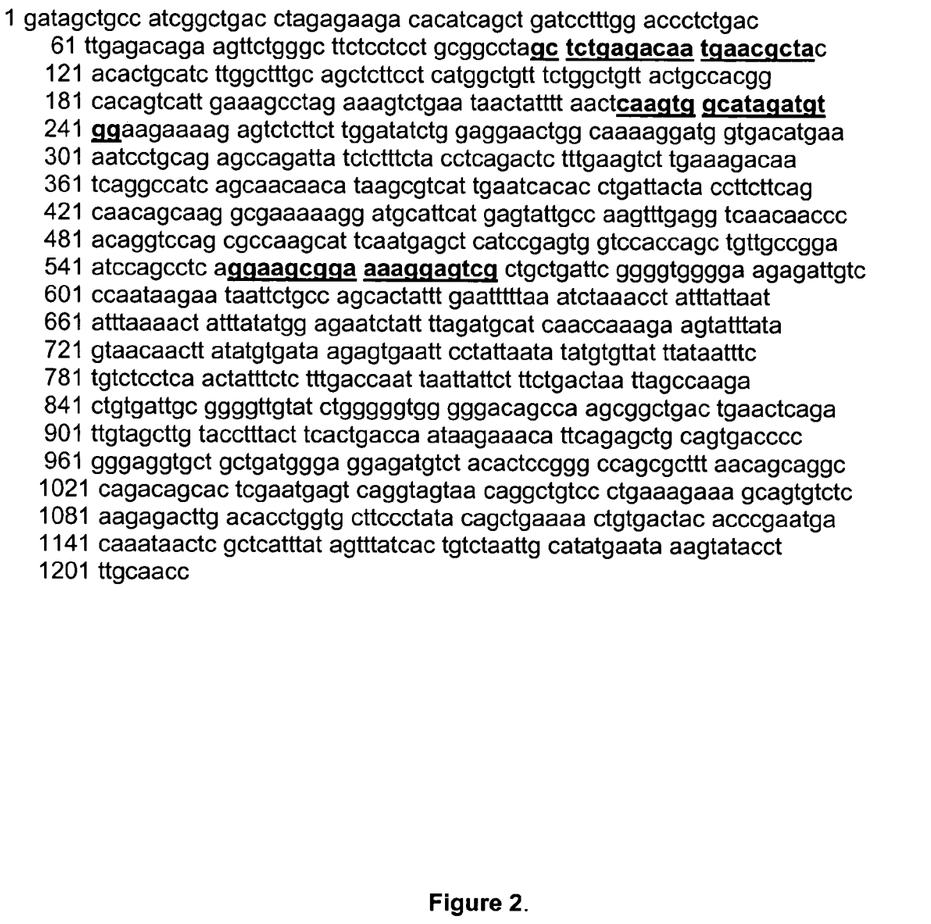
FIG. 2 is the DNA sequence of mIFN-γgene (SEQ ID NO: 1; GeneBank accession number NM_008337). The sequences corresponding to the primers used are underlined.
Figure 3:
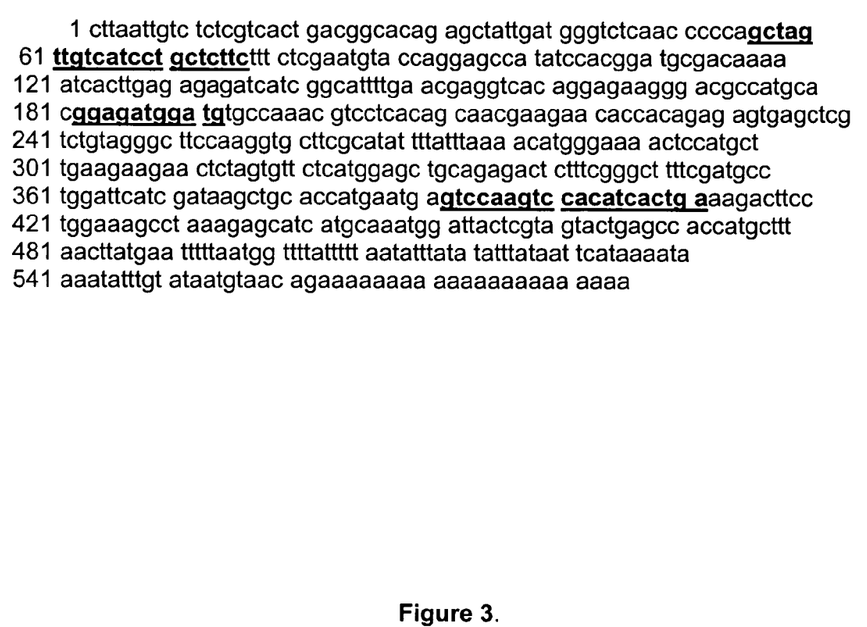
FIG. 3 is the DNA sequences mIL-4 (SEQ ID NO: 2; GeneBank accession number BC027514). The sequences corresponding to the primers used in qc-RT-PCR are underlined.

Primer designs in qc-RT-PCR for measuring gene expressions of IFN-γ and IL-4: The primers for interferon-γ and interleukin-4 were designed according to the sequences of GeneBank accession numbers NM_008337 and BC027514, respectively (Table 3A). For each gene, two pairs of primers, sharing the same 3' reverse primer but with different 5' forward primers were designed. In the first pair of primers, the DNA sequences of the 5' forward primer (called Standard Primer) are identical to a segment of the target gene. This pair of primers was used in PCR amplification to synthesize a nature length of DNA fragment (Standard Fragment). The Standard Fragment was cloned to form a "Standard Plasmid". In the second pair of primers, the 5' forward primer (called Competitor Primer) had a DNA sequences comprised of the Standard Primer immediately followed by a short segment of sequences that were identical to the gene sequences more than 100 base pairs downstream. This second pair of primers was used in PCR amplification to obtain a DNA fragment (Competitor Fragment) that had the same 5' and 3' sequence of the Standard Fragment, but was shorten by more than 100 base pairs. The Competitive Fragment was used to construct a Competitor Plasmid. The DNA sequences of mIFN-γ (see FIG. 2) and mIL-4 (see FIG. 3) are shown below. Primer designs, the predicted PCR product lengths are shown in Table 3A.

TABLE 3A

Primers used in qc-RT-PCR assay to determine levels of mIFN-γ and mIL-4 gene expression

|  |  | 5' forward primer | 3' reverse primer | PCR product length (DNA sequences) |
| --- | --- | --- | --- | --- |
| IFN-γ | Standard plasmid | Gctctgagacaatgaacgcta (SEQ ID NO: 3) | cgactccttttccgcttcc (SEQ ID NO: 4) | 473 b.p. (99 to 570) |
|  | Competitor plasmid | gctctgagacaatgaacgctacaagtggcatagatgtgg (SEQ ID NO: 5) | As Standard | 367 b.p. (99 to 119, 225 to 570) |
| IL-4 | Standard plasmid | gctagttgtcatcctgctcttc (SEQ ID NO: 6) | tcagtgatgtggacttggac (SEQ ID NO: 7) | 356 b.p. (56 to 411) |
|  | Competitor plasmid | Gctagttgtcatcctgctcttcggagatggatg (SEQ ID NO: 8) | As Standard | 231 b.p. (56 to 77, 182 to 411) |

Preparation of Standard Plasmid and Competitor Plasmid: Mice cDNA fragments of interferon-γ or interleukin-4, amplified with PCR kits and the Primers, were cloned into pGEM-T vectors (Promega, Madison, Wis.) to construct Standard Plasmids and Competitor Plasmids of these two genes. The Standard Plasmids and the Competitor Plasmids were all sequenced to confirm the accuracy of the inserted sequences.

Establish a standard curve: Following the principles of qc-RT-PCR method, known amounts of Competitor Plasmid were mixed into a series dilutions of known amount of Standard Plasmid, and the mixtures were used as DNA templates with a pair of Standard Primer and 3' reverse primer for PCR amplification. Both the Standard Fragment and the Competitor Fragment obtained from the PCR reactions were then used for ethidium-bromide gel electrophoresis. The correlations between the ratios of band intensities of the fragments and the ratios of the amount of plasmids used in each mixture were calculated of to establish a standard curve.

Gene expressions of interferon-γ and interleukin-4 in splenocytes determined by quantitative competitive-RT-PCR (qc-RT-PCR): After centrifugation, cell pellet of splenocytes was mixed with 1 ml Trizol reagent and then Trizol RNA Extract Kit isolated total RNA (Gibco, Life Technologies). The purity of total RNA of each sample was evaluated by the ratio of $A_{260\ nm}/A_{280\ nm}$. The mRNA was converted to cDNA with reverse transcriptase, and then analyzed by qc-PCR. The qc-PCR reaction was performed in a mixture of 1 μl standard primers (0.5 μg each of forward and reverse primers), 2.5 μl of 10×PCR buffer, 2.5 μl dNTP (2 mM), 0.1 μl DNA polymerase (5 U/μl), 0.5 μl sample cDNA and 0.5 μl of Competitor Plasmid, after the mixture was adjusted to a total volume of 25 μl with pure water. The PCR products were then analyzed with gel electrophoresis. The ethidium bromide density of each band in the gel was read with an Image Quant Densitometer, and the results were compared with the established standard curves to calculate the copy numbers of cDNA in the splenocyte samples.

Figure 4:
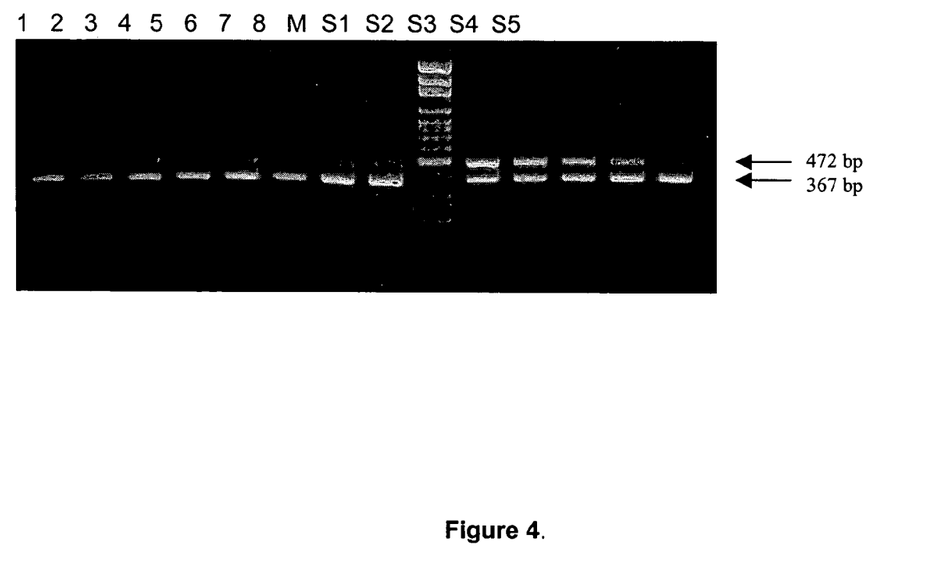
FIG. 4 is the gel electrophoresis of qc-RT-PCR products for determination of IFN-γmRNA expression level in mice splenocytes. Lanes 1-8 are PCR products using slenocytes cDNA samples and competitor plasmid as DNA templates. Lane M is markers (100 bp lader). Lanes S1-S5 are PCR products using Stander and Competitor Plasmid as DNA templates, for establishing a standard curve.
Figure 5:
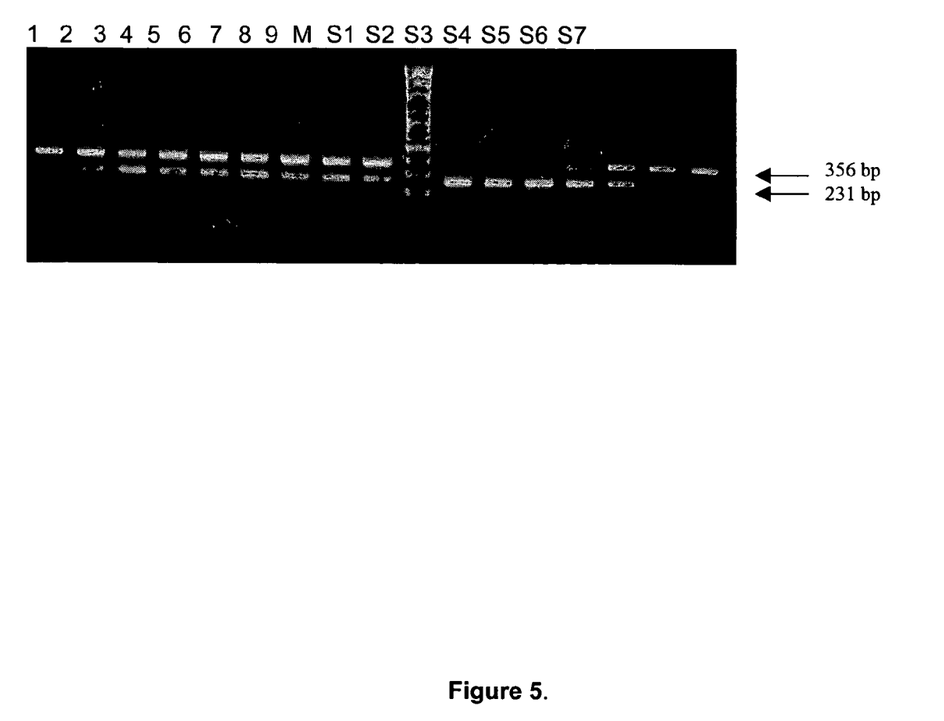
FIG. 5 is the gel electrophoresis of qc-RT-PCR products for determination of IL-4 mRNA expression level in mice splenocytes. Detection of IL-4 mRNA by qc-RT-PCR in mice splenocytes. Lanes 1-9 are PCR products using slenocytes cDNA samples and competitor plasmid as DNA templates. Lane M is markers (100 bp lader). Lanes S1-S7 are PCR products using Stander and Competitor Plasmid as DNA templates, for establishing a standard curve.

Results of Experiment 3: Anti-Allergic Activities of ZZ-ACE, Mice Model, Ex Vivo Anti-allergic activities of ZZ-ACE by Balancing Th1/Th2 immune response: After mice were treated with ZZ-ACE, splenocytes were harvested from the treated mice, and expression levels of IFN-γ and IL-4 genes were analyzed using qc-PCR. The results (Table 3B) showed that, in comparison to control, the gene expression level of IFN-γ ($p<0.05$) significantly increased and the gene expression level of IL-4 ($p<0.05$) significantly reduced in splenocytes of treated mice, with or without ConA stimulation. Since the ratio of gene expression of IFN-γ to IL-4 was significantly increased, ZZ-ACE may act beneficially to eliminate allergic reactions by modulating the Th1/Th2 balance. Thus, the results of this experiment indicated ZZ-ACE as having the potential to diminish allergic reactions by modulating the cytokine gene expressions in immune cells in mice, after 60-day's continuative administration of ZZ-ACE. Examples of gel electrophoresis pictures of PCR products of qc-RT-PCR for IFN-γ (FIG. 4) and IL-4 (FIG. 5) gene expression are shown below.

TABLE 3B

Level[1] of gene expression of IFN-γ and IL-4, with or without ConA stimulation, in splenocytes harvested from mice that were with or without drinking ZZ-ACE, and with or without asthma induction

|  | Water, no asthma | Water, asthma | ZZ-ACE, asthma |
|---|---|---|---|
| IFN-γ w/o ConA (copy/2 × $10^6$ cell) | $^a6.28 \times 10^3$ | $^b1.19 \times 10^5$ | $^c2.04 \times 10^5$ |
| IL-4 w/o ConA (copy/2 × $10^6$ cell) | $^a2.04 \times 10^5$ | $^b24.9 \times 10^5$ | $^c8.61 \times 10^5$ |
| [2]IFN-γ/IL-4 w/o ConA | $^a0.039$ | $^a0.046$ | $^b0.242$ |
| IFN-γ w/ConA (copy/2 × $10^6$ cell) | $^a1.26 \times 10^4$ | $^a1.59 \times 10^5$ | $^b6.34 \times 10^5$ |

TABLE 3B-continued

Level[1] of gene expression of IFN-γ and IL-4, with or without ConA stimulation, in splenocytes harvested from mice that were with or without drinking ZZ-ACE, and with or without asthma induction

|  | Water, no asthma | Water, asthma | ZZ-ACE, asthma |
|---|---|---|---|
| IL-4 w/Con A (copy/2 × $10^6$ cell) | $^a5.29 \times 10^5$ | $^b5.68 \times 10^6$ | $^a1.49 \times 10^6$ |
| [2]IFN-γ/IL-4 w/ConA | $^a0.026$ | $^a0.032$ | $^b0.378$ |

[1]different superscripts in the same row indicate significant difference ($p < 0.05$).
[2]values were calculated by first calculating the ratio of IFN-γ/IL-4 from each mouse, then the ratios were averaged.

Experiment 4: Identification of Zerumbone as an Active Compound Modulates the Balance of Th1/Th2 Immune Responses Methods of Experiment 4:

Active Compound Identification: Dried ZZ root was first extracted with ethanol (Ethanol Extract), than the extract was chromatographically further purified with Silica gel and PLC, and assayed with in vitro bioactive screening (procedures described below in Experiments 4A to 4E) to identify purification fraction that contains strong anti-allergic activities (results described below in Experiments 4A to 4E). Active compound was then isolated from the identified active fractions.

Figure 6:
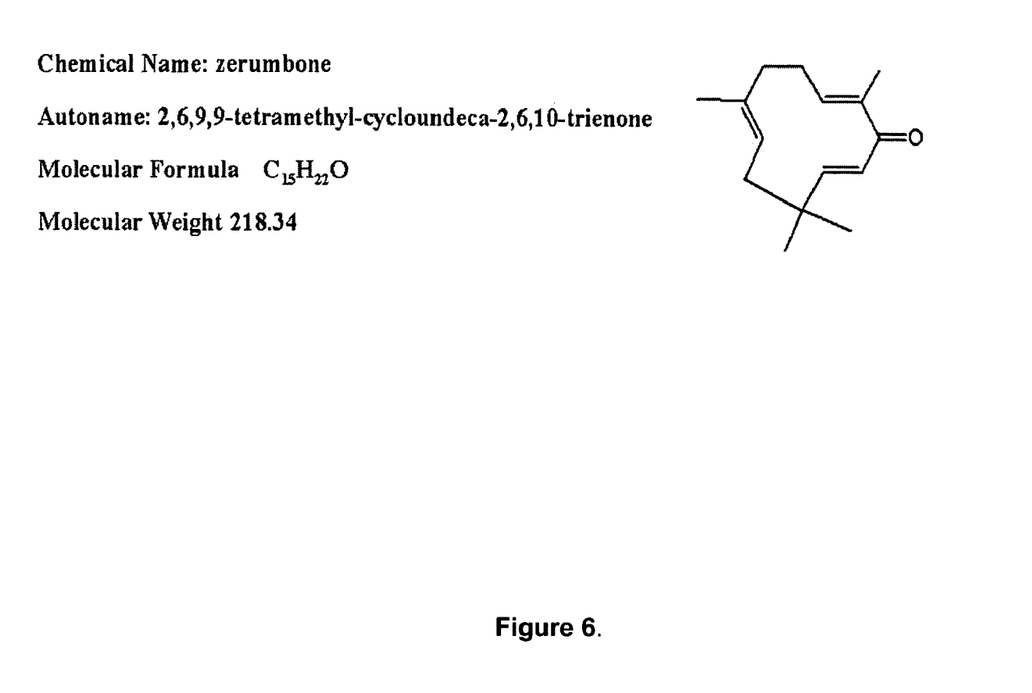
FIG. 6 is the chemical structure of Zerumbone

Result of Experiment 4: Identification of Zerumbone as an Active Compound Modulates the Balance of Th1/Th2 Immune Responses Active Compound Identification: The compound in the active fractions was identified as zerumbone. See FIG. 6 for the structure of zerumbone.

4A: Effects of ZZ Samples on Level of Eotaxin Secretion by IL-13/TNF-α Stimulated Human BEAS-2B Cells Methods of Experiment 4A:

Cell culture, treatment with ZZ samples, and stimulation for eotaxin expression: SV40 transformed human bronchial epithelial cells BEAS-2B were seeded in 96-well plates with F12/DMEM medium and incubated at 37° C. to confluence. Cells were then treated with different concentrations of ZZ samples. After 20 minutes treatment, cells were stimulated with 50 ng/ml of human IL-13 (Peprotech, 200-13) and 100 ng/ml of human TNF-α (Peprotech, 300-01A) at 37° C. for 22 hours. Culture media were collected and their eotaxin concentrations were measured.

ELISA Assay for Cytokine Eotaxin: Eotaxin concentration was determined by using Opt EIA Set; human eotaxin was from Pharmingen; 2623KI. 96-well plates were from IWAKI, 3801-096. Assays were performed according to the instructions provided by the manufacturer.

Results of Experiment 4A:

After SV40 transformed human bronchial epithelial cells BEAS-2B were treatment with ZZ samples, and stimulated with human TNF-α to express eotaxin, the culture media were collected and their eotaxin concentrations were measured with an ELISA kit. The results were summarized in Table 4A. Eotaxin inhibition activity was found to be rich in Ethanol Extract fraction, and was even richer in a fraction with Zerumbone.

TABLE 4A

Effects of ZZ samples on level of Eotaxin secretion by IL-13/TNF-α stimulated human BEAS-2B cells

|  | Control, no ZZ treatment | Ethanol Extract (50 µg/ml) | Crude Zerumbone (50 µg/ml) |
|---|---|---|---|
| Eotaxin released, as % of control | 100 | 23 | 12 |

4B: Effects of ZZ Samples on Level of TNF-α Secretion by Murine Peritoneal Macrophages Method of Experiment 4B:

Cell culture: Mouse peritoneal macrophages were elicited by i.p. (intraperitoneally) injection of 1 ml of 4% Brewer's thioglycolate medium (Sigma, B2551) into peritoneal cavity of male BALB/c mice (aged 6-10 wk). Peritoneal cells were obtained 7 days after injection by peritoneal lavage with ice-cold RPMI-1640 medium.

Drug treatment: Murine peritoneal macrophages ($1\times10^5$) were seeded in flat-bottom 96-well plates with RPMI-1640 medium. Cells were treated with different concentrations of ZZ-ACE samples for 20 minutes, then were stimulated with 1.5 µg/ml of LPS (Lipopolysaccharide) (Sigma, L-2880) for further 22 hours, before media were collected for TNFα assay.

TNF-α ELISA assay: TNF-α was determined using R&D mouse TNF-α ELISA (Duoset, DY410) following the procedures recommended by the manufacturer.

Results of Experiment 4B:

When mouse peritoneal macrophages were treated with different concentrations of ZZ-ACE samples in vitro, then stimulated LPS before media were collected for TNFα assay, the results showed that both the ZZ-ACE and a purification fraction that is rich in Zerumbone have inhibition activities on TNFα released.

TABLE 4B

Effects of ZZ samples on level of TNF-α secretion by LPS stimulated murine peritoneal macrophages.

|  | Control, no ZZ treatment | ZZ-ACE (5 µg/ml) | Crude Zerumbone (5 µg/ml) |
|---|---|---|---|
| TNF-α released, as % of control | 100 | 63 | 55 |

4C: In Vitro Effects of ZZ Samples on Level of B Cell Proliferation of LPS Stimulated Mouse Splenocytes Method of Experiment 4C:

Preparation of splenocytes: Mouse spleens were collected from BALB/c male mice (8 to 12 week of age). Spleens were grinded with a plunger of a 10-ml syringe, in 10 ml of RPMI-1640 medium (GIBCO Cat. No. 23400-013) supplemented with 10% (v/v) fetal calf serum (FCS; Biological Industries, 04-001-1B), 5 µg/ml of Gentamycine (Biological Industries, 03-035-1B), 1 µg/ml of kanamycine (Biological Industries, 03-049-1B), 1.2 mM of sodium pyruvate (Gibco, 11360-070), 0.12 mM of non-essential amino acid (Gibco, 11140-050), 0.2 mM of 2-mercaptoethanol (Sigma, M7522), and 2 g/l of sodium bicarbonate (Sigma, S5761). Then 15 ml of ACK lysis buffer (0.15 M $NH_4Cl$, 10 mM KHCO3, 0.1 mM $Na_2EDTA$, pH 7.2) was added to lyse the red blood cells. After ACK lysis buffer treatment, the splenocytes were collected by centrifugation at 1500 rpm for 10 min at 4□, then were washed with 10 ml cell culture medium, and finally resuspended into cultured medium.

The Drug Effect on B Cell Proliferation of Splenocytes from BALB/c Mouse

Drug treatment on slenocytes, and stimulation for B cell proliferation: Splenocytes ($1.5\times10^5$) were seeded in flat-bottom 96-well plates with RPMI-1640 medium with 10% FCS. Splenocytes were treated with the various concentrations of ZZ samples for 2 h at 37° C., then were stimulated with 15 µg/ml of LPS (Sigma, L2880) in RPMI-1640 medium containing 10%(v/v) fetal calf serum at 37° C. for 66 h to encourage B cells proliferation, before assay.

Proliferation assay for B cells: Proliferation was determined using Roche BrdU ELISA kit (Roche, 1647229). Cells in 96-well plate were first treated with 100 µM of BrdU at 37° C. for 6 h. The plates were then centrifuged at 1500 rpm for 10 min at 4□. Supernatants were moved without disturbing the cells. Plates were incubated at 60□ for 1 h, and then 200 µl per well of FixDenat were added. After 30 min incubation at RT, FixDenat was discarded, 300 µl per well of blocking solution was added. The plates were kept at RT for 1 h, washed three times with 300 µl per well of washing buffer, and then 100 µl per well of anti-BrdU-POD was added. After incubation at RT for 1 h the plates were washed four times with washing buffer and then added 100 µl per well of substrate and cultured at RT for 5 min in the dark. Reactions were terminated by addition of 25 µl of stock solution/well and OD was measured by using a microplate reader at 450 nm.

Results of Experiment 4C:

TABLE 4C

In vitro Effects of ZZ samples on level of B cell proliferation of LPS stimulated mouse splenocytes

|  | Control, no ZZ treatment | Water Extract (5 µg/ml) | Crude Zerumbone (5 µg/ml) |
|---|---|---|---|
| B cell proliferation, as % of control | 100 | 62 | 60 |

4D: In Vitro Effects of ZZ Samples on Level of INF-γ Secretion bv ConA Stimulated Mouse Splenocytes Methods of Experiment 4D:

Splenocyte preparation and Drug treatment: Splenocytes being prepared (see experiment 4C) and diluted to $6\times10^5$ cells/100 µl, were seeded in flat-bottom 96-well plates with RPMI-1640 medium with 10% FCS. Splenocytes were then treated with various concentrations of ZZ samples (30 µl) for 2 hr at 37° C., and finally stimulated with 1 µg/ml of concanavalin A (conA) for 18 h. IFN-v concentrations in the media were determined by ELISA assay, and cell viability was measured by MTT assay.

IFN-gamma ELISA: Mouse IFN-gamma was determined by using R&D mouse IFN-gamma (Duoset, DY485) kit. Elisa assay was performed according to the procedures recommended by the manufacturer.

Results of Experiment 4D:

The Effects ZZ samples on the level of INF-γ secretion by ConA stimulated mouse splenocytes were summarized in Table 4D. Both ZZ-ACE and the Ethanol Extraction fractions showed ability to increase IFN-y concentration in the culture media.

TABLE 4D

In vitro effects of ZZ samples on level of INF-γ secretion by ConA stimulated mouse splenocytes

|  | Control, no ZZ treatment | ZZ-ACE (50 μg/ml) | Ethanol Extract (50 μg/ml) |
|---|---|---|---|
| IFN-γ released as % of control | 100 | 132 | 127 |

4E: Effects of ZZ Samples on Level of IL-4 Secretion by PMA/A23187 Stimulated Mouse EL-4 Cell Methods of Experiment 4E:

Cell culture: EL-4 cells were cultured in 75-cm$^2$ culture flask in RPMI-1640 medium supplemented with 10% (v/v) fetal calf serum, 5 μg/ml of Gentamycine (Biological Industries), 1 μg/ml of kanamycine (Biological Industries), 1.2 mM of sodium pyruvate, 0.12 mM of non-essential amino acid, 0.2 mM of 2-mercaptoethanol, 2 g/l of sodium bicarbonate in 5% $CO_2$ at 37° C.

Drug treatment: EL-4 cells (1×10$^4$ cells/100 μl) were seeded in flat-bottom 96-well plates with RPMI-1640 medium with 10% FCS. Cells were treated with various concentrations of ZZ-ACE sample (30 μl) for 2 hours at 37° C., then were stimulated with 1.5 ng/well of PMA and 15 ng/well of A23187 in RPMI-1640 medium with 10% (v/v) fetal calf serum (total volume 150 μl) at 37° C. for 22 hours. Levels of IL-4 secretion in the cell-free supernatants were determined by ELISA assay and cell viability was measured by MTT assay.

IL-4 ELISA: IL-4 was determined using R&D mouse IL-4 ELISA (Duoset, DY404). 96-well plates (IWAKI, 3801-096) were coated with 100 μl/well of the capture antibody (4 μg/ml in PBS) and incubated overnight at room temperature. The plates were then washed three times with washing buffer (PBS containing 0.05% Tween 20) and blocked by incubating with 300 μl of blocking buffer/well (PBS containing 1% bovine serum albumin and 5% sucrose) at room temperature for 1 h. The plates were washed three times with washing buffer before 100 μl of test or standards were added to the wells. The plates were incubated at room temperature for 2 h, washed, and incubated with detection antibody [100 μl of 200 ng/ml in Reagent Diluent (PBS containing 1% bovine serum albumin)/well] at room temperature for 2 h. After washing, 100 μl of Streptavidin-HRP was added to each well, incubated at room temperature for 20 min, and, after washing, incubated with 100 μl of TMB (Clinical) per well for 20 min. Reactions were terminated by addition of 100 μl of 1N HCl/well, and measured OD by using a microplate reader at 450 nm.

Results of Experiment 4E:

TABLE 4E

Effects of ZZ samples on IL-4 secretion by PMA/A23187 stimulated mouse EL-4 cell

|  | Control, no ZZ treatment | Ethanol Extract (50 μg/ml) | Crude Zerumbone (50 μg/ml) |
|---|---|---|---|
| IL-4 released as % of control | 100 | 25 | 12 |

Experiment 5: Human Volunteers Using ZZ-ACE for Allergic Rhinitis

Five volunteers took ZZ-ACE to treat allergic rhinitis. Their experiences are summarized here.

Volunteer A:

Mr. Wen had severe allergic rhinitis for years. To treat his rhinitis, daily, freshly harvested ZZ root (before drying) 300 gm was cooked in water and the soup was taken. The treatment was repeated for seven days as one treatment course. His symptoms were significantly reduced at the end of the treatment. Three months later, when symptoms returned, the treatment course was repeated successfully.

Volunteer B:

Another Mr. Wen (father of volunteer A), followed the treatment course of Volunteer A, has successfully reduced his allergic rhinitis symptoms. Treatment courses were repeated later whenever allergy seasons arrived.

Volunteer C:

Mr. Lee cooked 1000 gm of wet fresh ZZ root, and refrigerated the soup in sealed containers. He drank about ¼ of the soup daily for four days to treat his allergic rhinitis. The result was satisfactory. He repeated the same treatment course successfully again when the symptoms returned later.

Volunteer D:

Mr. Du took ZZ capsules for two months, 6 capsules in the morning and 6 capsules in the evening, daily, to treat very severe allergic rhinitis successfully.

The ZZ capsules were prepared by the following procedures. Dried ZZ root was cooked in 10 times of water (weight to weight ratio). The soup was concentrated approximately 5 fold then dried down as granules using starch as excipient. The granules were used to fill capsules. Each capsule contains 0.5 gm of granules that is equivalent to about 2.0 gm of dried ZZ root, or about 20 gm of freshly harvested ZZ root.

Volunteer E:

The same batch of ZZ capsules used by Volunteer D was also used to treat Volunteer E, Mr. Huang for about 180 day, 3 capsules per day. During the 180 days, the volunteer experienced less allergic problem than before.

The invention is not limited by the embodiments described above which are presented as examples only but can be modified in various ways within the scope of protection defined by the appended patent claims.

REFERENCES

1. Wenzel S E. *The role of leukotrienes in asthma*. Prostaglandins Leukot Essent Fatty Acids 2003; 69:145-55.

2. Leff A R. *Regulation of leukotrienes in the management of asthma: biology and clinical therapy*. Annu Rev Med 2001; 52:1-14.

3. Aizawa T, Tamura G, Ohtsu H, Takishima T. *Eosinophil and neutrophil production of leukotriene C4 and B4: comparison of cells from asthmatic subjects and healthy donors*. Ann Allergy 1990; 64:287-92.

4. Davern T J, Bass N M. *Leukotriene antagonists*. Clin Liver Dis 2003; 7(2):501-12, viii.

5. Beghe B, Barton S, Rorke S, Peng Q, Sayers I, Gaunt T, Keith T, Clough J, Holgate S, Holloway J. *Polymorphisms in* the interleukin-4 and interleukin-4 receptor alpha chain genes confer susceptibility to asthma and atopy in a Caucasian population. Clin Exp Allergy 2003; 33:1111-1117.

6. Shirai T, Suzuki K, Inui N, Suda T, Chida K, Nakamura H. *Th1/Th2 profile in peripheral blood in atopic cough and atopic asthma*. Clin Exp Allergy 2003; 33:84-9.

7. Lee Y C, Lee K H, Lee H B, Rhee Y K. *Serum levels of interleukins (IL)-4, IL-5, IL-13, and interferon-gamma in acute asthma*. J Asthma 2001; 38:665-71.

8. Kalin P. *The Common Butterbur (Petasites hybridus)—Portrait of a Medicinal Herb*. Forsch Komplementarmed Klass Naturheilkd 2003; 10 Suppl 1:41-4.

9. Vimala S, Norhanom A W, Yadav M. *Anti-tumour promoter activity in Malaysian ginger rhizobia used in traditional medicine*. Br J Cancer 1999; 80:110-6.

10. Murakami A, Takahashi D, Kinoshita T, Koshimizu K, Kim H W, Yoshihiro A, Nakamura Y, Jiwajinda S, Terao J, Ohigashi H. *Zerumbone, a Southeast Asian ginger sesquiterpene, markedly suppresses free radical generation, proinflammatory protein production, and cancer cell proliferation accompanied by apoptosis: the alpha, beta-unsaturated carbonyl group is a prerequisite*. Carcinogenesis 2002; 23:795-802. Comment in: Carcinogenesis 2002; 23:1961; author reply 1963.

We claim:

1. A method of treating an allergic disorder comprising administering an effective amount of a solvent extract from the root of *Zingiber zerumbet* Sm to a subject suffering from the allergic disorder.

2. The method of claim 1 wherein the allergic disorder is selected from the group consisting of allergic rhinitis, asthma and eczema.

3. The method of claim 1 wherein said treating comprises regulating the balance between Th1 and Th2 immune responses.

4. The method of claim 3 wherein said regulating comprises up-regulating the concentration of IFN-γ or down-regulating inflammatory mediators TNF-α, IL-4, and eotaxin.

5. The method of claim 4, where the solvent extract comprises zerumbone.

6. The method of claim 1, wherein the extract comprises 5,7-Dihydroxy-2-(4-hydroxy-phenyl)-3-methoxy-chromen-4-one.

7. The method of claim 1, wherein the subject comprises a mouse or a human.

* * * * *

UNITED STATES PATENT AND TRADEMARK OFFICE
CERTIFICATE OF CORRECTION

PATENT NO. : 7,588,788 B2  Page 1 of 1
APPLICATION NO. : 11/184678
DATED : September 15, 2009
INVENTOR(S) : Chaung et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 392 days.

Signed and Sealed this

Fourteenth Day of December, 2010

David J. Kappos
*Director of the United States Patent and Trademark Office*

SEQUENCE LISTING

```
<160> NUMBER OF SEQ ID NOS: 8

<210> SEQ ID NO 1
<211> LENGTH: 1208
<212> TYPE: DNA
<213> ORGANISM: Mus musculus

<400> SEQUENCE: 1
gatagctgcc atcggctgac ctagagaaga cacatcagct gatcctttgg accctctgac      60
ttgagacaga agttctgggc ttctcctcct gcggcctagc tctgagacaa tgaacgctac     120
acactgcatc ttggctttgc agctcttcct catggctgtt tctggctgtt actgccacgg     180
cacagtcatt gaaagcctag aaagtctgaa taactatttt aactcaagtg gcatagatgt     240
ggaagaaaag agtctcttct tggatatctg gaggaactgg caaaaggatg gtgacatgaa     300
aatcctgcag agccagatta tctctttcta cctcagactc tttgaagtct tgaaagacaa     360
tcaggccatc agcaacaaca taagcgtcat tgaatcacac ctgattacta ccttcttcag     420
caacagcaag gcgaaaaagg atgcattcat gagtattgcc aagtttgagg tcaacaaccc     480
acaggtccag cgccaagcat tcaatgagct catccgagtg gtccaccagc tgttgccgga     540
atccagcctc aggaagcgga aaaggagtcg ctgctgattc ggggtgggga agagattgtc     600
ccaataagaa taattctgcc agcactattt gaatttttaa atctaaacct atttattaat     660
atttaaaact atttatatgg agaatctatt ttagatgcat caaccaaaga agtatttata     720
gtaacaactt atatgtgata agagtgaatt cctattaata tatgtgttat ttataatttc     780
tgtctcctca actatttctc tttgaccaat taattattct ttctgactaa ttagccaaga     840
ctgtgattgc ggggttgtat ctgggggtgg gggacagcca agcggctgac tgaactcaga     900
ttgtagcttg tacctttact tcactgacca ataagaaaca ttcagagctg cagtgacccc     960
gggaggtgct gctgatggga ggagatgtct acactccggg ccagcgcttt aacagcaggc    1020
cagacagcac tcgaatgagt caggtagtaa caggctgtcc ctgaaagaaa gcagtgtctc    1080
aagagacttg acacctggtg cttccctata cagctgaaaa ctgtgactac acccgaatga    1140
caaataactc gctcatttat agtttatcac tgtctaattg catatgaata aagtatacct    1200
ttgcaacc                                                            1208

<210> SEQ ID NO 2
<211> LENGTH: 584
<212> TYPE: DNA
<213> ORGANISM: Mus musculus

<400> SEQUENCE: 2
cttaattgtc tctcgtcact gacggcacag agctattgat gggtctcaac ccccagctag      60
```

-continued

```
ttgtcatcct gctcttcttt ctcgaatgta ccaggagcca tatccacgga tgcgacaaaa      120
atcacttgag agagatcatc ggcattttga acgaggtcac aggagaaggg acgccatgca      180
cggagatgga tgtgccaaac gtcctcacag caacgaagaa caccacagag agtgagctcg      240
tctgtagggc ttccaaggtg cttcgcatat tttatttaaa acatgggaaa actccatgct      300
tgaagaagaa ctctagtgtt ctcatggagc tgcagagact ctttcgggct tttcgatgcc      360
tggattcatc gataagctgc accatgaatg agtccaagtc cacatcactg aaagacttcc      420
tggaaagcct aaagagcatc atgcaaatgg attactcgta gtactgagcc accatgcttt      480
aacttatgaa tttttaatgg ttttattttt aatatttata tatttataat tcataaaata      540
aaatatttgt ataatgtaac agaaaaaaaa aaaaaaaaa aaaa                        584
```

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gctctgagac aatgaacgct a                                                 21

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cgactccttt tccgcttcc                                                    19

<210> SEQ ID NO 5
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gctctgagac aatgaacgct acaagtggca tagatgtgg                              39

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gctagttgtc atcctgctct tc                                                22

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer -continued

```
<400> SEQUENCE: 7
tcagtgatgt ggacttggac                                                      20

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gctagttgtc atcctgctct tcggagatgg atg                                       33
```